(12) United States Patent
Lin et al.

(10) Patent No.: US 8,406,841 B2
(45) Date of Patent: Mar. 26, 2013

(54) DRY ELECTRODE FOR BIOMEDICAL SIGNAL MEASURING SENSOR

(75) Inventors: Chin-Teng Lin, Hsinchu (TW); Lun-De Liao, Hsinchu (TW)

(73) Assignee: National Chiao Tung University, Hsinchu (TW)

( * ) Notice: Subject to any disclaimer, the term of this patent is extended or adjusted under 35 U.S.C. 154(b) by 346 days.

(21) Appl. No.: 12/960,868

(22) Filed: Dec. 6, 2010

(65) Prior Publication Data

US 2012/0046535 A1 Feb. 23, 2012

(30) Foreign Application Priority Data

Aug. 20, 2010 (TW) ................................ 99128042 A

(51) Int. Cl.
*A61B 5/04* (2006.01)
*A61B 5/0478* (2006.01)
(52) U.S. Cl. .......................... 600/372; 600/383; 600/395
(58) Field of Classification Search ........... 600/372.383, 600/395
See application file for complete search history.

(56) References Cited

U.S. PATENT DOCUMENTS

| | | | | |
|---|---|---|---|---|
| 4,088,133 | A | * | 5/1978 | Twentier .......................... 606/32 |
| 5,003,978 | A | * | 4/1991 | Dunseath, Jr. ................. 600/391 |
| 2007/0249952 | A1 | * | 10/2007 | Rubin et al. ................... 600/544 |

* cited by examiner

*Primary Examiner* — Lee S Cohen
(74) *Attorney, Agent, or Firm* — Che-Yang Chen; Law Office of Michael Chen

(57) ABSTRACT

A dry electrode for biomedical signal measuring sensor includes a conductive sponge, a conductive fabric, and a thin metal film. The conductive fabric covers the whole conductive sponge, and the thin metal film is disposed on one face of the conductive fabric opposite to the conductive sponge. When using the dry electrode in measuring biomedical signal, it is not necessary to apply a conductive gel on a patient's skin, at where the biomedical signal is to be measured. Without the need of applying the conductive gel, the dry electrode is readily for measuring biomedical signal at any time and can be conveniently used in measuring signal over a long period of time without the problem of an attenuated signal due to gradually becoming dried conductive gel.

8 Claims, 10 Drawing Sheets

DRY ELECTRODE FOR BIOMEDICAL SIGNAL MEASURING SENSOR

FIELD OF THE INVENTION

The present invention relates to an electrode, and more particularly to a dry electrode for biomedical signal measuring sensor.

BACKGROUND OF THE INVENTION

Currently, instruments for measuring biomedical signals are very popular medical devices and can be applied in military field, biomedical field, man-machine system field, and so on. Biomedical signal measuring instruments may include electroencephalograph (EEG), electrocardiograph (ECG), etc. The EEG records the electrical activity of neurons within the brain via electrodes placed on the scalp. Since the EEG is a non-invasive instrument and is able to reflect the activity of brain cells within a few milliseconds (ms), it has been widely applied in medical diagnosis and neurobiological research.

Traditionally, the electrode for the EEG is a wet electrode. Before placing the wet electrode on a patient's skin, it is necessary to apply a layer of conductive gel on the patient's skin. The conductive gel might cause discomfort to some patients, such as allergy or swelling. And, the conductive gel tends to become dried with time and therefore has lowered electric conductivity when the measurement has continued for a longer period of time. That is, the wet electrode requiring the application of conductive gel could not be used over a long period of time in measuring the biomedical signal. Further, when the wet electrode is to be placed on an area with densely distributed hair for measuring biomedical signal, the hair must be properly shaved off the skin in advance to ensure that the wet electrode can measure accurate biomedical signal. Moreover, in the conventional way of measuring the brain electric signal, several tens of wet electrodes are needed at the same time. Since not all the wet electrodes have the same electric conductivity, a lot of time will be consumed in necessary pre-process and time adjustment before the measurement can start.

Compared to the wet electrode, the dry electrode applied in biomedical signal measurement is more convenient for use and provides more advantages. However, the current dry electrode is manufactured through microstructure process, such as micro-electro-mechanical system (MEMS), or using carbon nanotubes. Dry electrodes with such structures tend to break in use, and could not be used at body areas with hair. These disadvantages prevent the dry electrode from being widely accepted in the measuring of biomedical signal.

SUMMARY OF THE INVENTION

A primary object of the present invention is to provide a dry electrode for biomedical signal measuring sensor, so that biomedical signal can be measured with the dry electrode at any time without the need of applying any conductive gel on the patient's skin or shaving hair off the patient's skin, and the measured signal will not attenuate with time due to dried conductive gel.

To achieve the above and other objects, the dry electrode for biomedical signal measuring sensor according to the present invention includes a conductive sponge, a conductive fabric, and a thin metal film. The conductive fabric covers the whole conductive sponge therein, and the thin metal film is disposed on one face of the conductive fabric opposite to the conductive sponge to facilitate subsequent connection of the dry electrode to a digital signal pickup device. The thin metal film can be formed of a metal material with good electric conductivity, such as gold, to enable upgraded conduction performance.

In the dry electrode of the present invention, the conductive sponge can be made of a urethane material, the thin metal film can be gold, and the conductive fabric can be in the form of a honeycomb net or a fabric coated with metal having good electrical conductivity. The metal with good electrical conductivity can be platinum, nickel, copper, aluminum, iron, or silver; and the fabric can be a piece of taffeta.

In another embodiment of the present invention, the dry electrode can further include an enclosure being provided around the conductive fabric that has been covered over the whole conductive sponge. For example, in the case the conductive sponge is a right cuboid, the conductive fabric is used to cover all the six faces of the conductive sponge, and then, the enclosure is provided around the conductive fabric to cover four lateral faces of the right cuboid with the top and bottom faces of the right cuboid exposed from the enclosure. The thin metal film is disposed on the conductive fabric at the top face of the right cuboid for connecting to the digital signal pickup device. The conductive fabric at the bottom face of the right cuboid is in direct contact with a patient's skin. The enclosure can be made of an electromagnetic-shielding material, such as a soft silica gel material, to allow the dry electrode of the present invention to fitly attach to the patient's skin.

With the above arrangements, the dry electrode for biomedical signal measuring sensor according to the present invention has the following one or more advantages:

(1) The conductive sponge and the conductive fabric for the dry electrode have relatively high pliability for closely attaching to the patient's body area to be measured, and the signal measured when the patient is in movement can still provide very good measurement characteristics.

(2) The conductive fabric for the dry electrode of the present invention is provided using a conventional cloth fabric mixing process to have relatively high pliability, and can therefore improve the drawback of the conventional rigid electrode.

(3) When using the dry electrode of the present invention, it is not necessary to apply any conductive gel on the patient's skin or remove the stratum corneum from the patient's skin, and therefore would not cause any discomfort, such as allergy or swelling, to the patient. The dry electrode can also be directly placed on the patient's body area with densely distributed hair without the need of invading into the patient's skin or shaving hair off the patient's skin, so that the biomedical signal can be readily measured at any time.

(4) Since it is not necessary to apply any conductive gel on the patient's skin when using the dry electrode of the present invention to measure the biomedical signal, the measured signal is stable without being subject to attenuation due to dried conductive gel.

(5) The dry electrode of the present invention can be manufactured with very simple process at low manufacturing cost, and is therefore very suitable for mass-production.

(6) The dry electrode can include an enclosure being provided around the conductive fabric that has been covered over the whole conductive sponge. The enclosure can be designed as a removable enclosure to allow replacement of the conductive sponge and the conductive fabric at any time.

(7) The dry electrode of the present invention can be used to measure not only brain electric signal and heart electric signal, but also other biomedical signals, such as muscle electric signal and eye movement signal.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENTS

Figure 1:
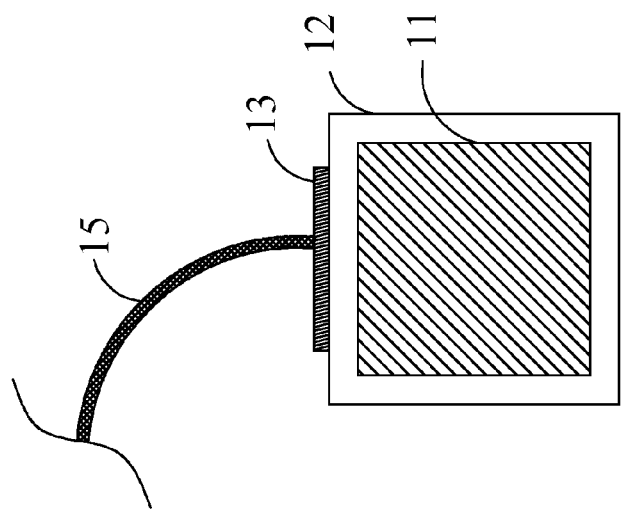
FIG. 1 is a sectional view of a dry electrode for biomedical signal measuring sensor according to a first embodiment of the present invention.

Please refer to FIG. 1 that is a sectional view of a dry electrode for biomedical signal measuring sensor according to a first embodiment of the present invention. As shown, the dry electrode according to the first embodiment includes an electrically conductive sponge 11, an electrically conductive fabric 12 and a thin metal film 13 all with good electrical conductivity. The conductive fabric 12 covers the whole conductive sponge 11, and the thin metal film 13 is disposed on one face of the conductive fabric 12 opposite to the conductive sponge 11 to facilitate subsequent connection of the dry electrode to a digital signal pickup device. The conductive fabric 12 can have electrical conductivity higher than that of the conductive sponge 11, and is preferably in the form of a honeycomb net. The conductive fabric 12 can be otherwise a fabric coated with a layer of metal with good electrical conductivity. Metals with good conductivity include, for example, platinum, nickel, copper, aluminum, iron and silver. The fabric can be a piece of taffeta. The thin metal film 13 can be gold to enable upgraded overall electrical conducting effect.

Figure 2:
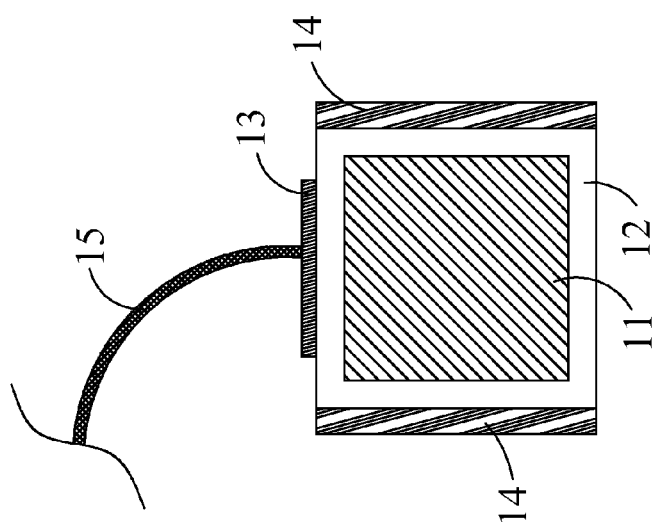
FIG. 2 is a sectional view of a dry electrode for biomedical signal measuring sensor according to a second embodiment of the present invention.

FIG. 2 shows a dry electrode according to a second embodiment of the present invention. As shown, in the second embodiment, the dry electrode further includes an enclosure 14 provided around the conductive fabric 12 that is covered on the whole conductive sponge 11. For example, in the case the conductive sponge 11 is a right cuboid, the conductive fabric 12 is used to cover all the six faces of the conductive sponge 11. And then, the enclosure 14 is provided around the conductive fabric 12 to cover four lateral faces of the right cuboid with the top and bottom faces of the right cuboid exposed from the enclosure 14. The thin metal film 13 is disposed on the conductive fabric 12 at the top face of the right cuboid for connecting to a cable 15 or a general electric wire for a biomedical signal measuring instrument. The conductive fabric 12 at the bottom face of the right cuboid is in direct contact with a patient's skin, at where the biomedical signal is measured. The enclosure 14 can be made of an electromagnetic-shielding material, and is preferably made of a soft silica gel material to allow the dry electrode of the present invention to fitly attach to the patient's skin, so as to ensure accurate measurement.

Generally speaking, the dry electrode of the present invention has dimensions smaller than a 25-cent (i.e. a quarter) coin used in U.S. The dry electrode of the present invention can be, for example, shaped as a right cuboid having dimensions of 14×8×8 mm without being limited thereto. After connecting the thin metal film 13 to the cable 15 or the general electric wire for the biomedical signal measuring instrument, the dry electrode is ready for use.

To prove that the dry electrode of the present invention is superior to the conventional wet electrode in practical use, signal quality check, impedance measurement and motion artifact test are conducted for the dry electrode of the present invention, and signals measured with the dry electrode of the present invention are compared with those measured with the conventional wet electrode.

In the illustrated embodiments of the dry electrode according to the present invention, the conductive sponge 11 is made of a urethane material having a compression set ranged between 5% and 10%; the conductive fabric is made of 0.2 mm thick taffeta and the taffeta is coated at both sides with Ni/Cu to form electrical contacts; and the thin metal film is formed of gold and has a thickness about 0.2 nm to serve as an adhesion layer for subsequent connection to a brain wave signal pickup device. And, the following tests are conducted.

(A) Signal Quality Check for the Dry Electrode of the Present Invention

Figure 3:
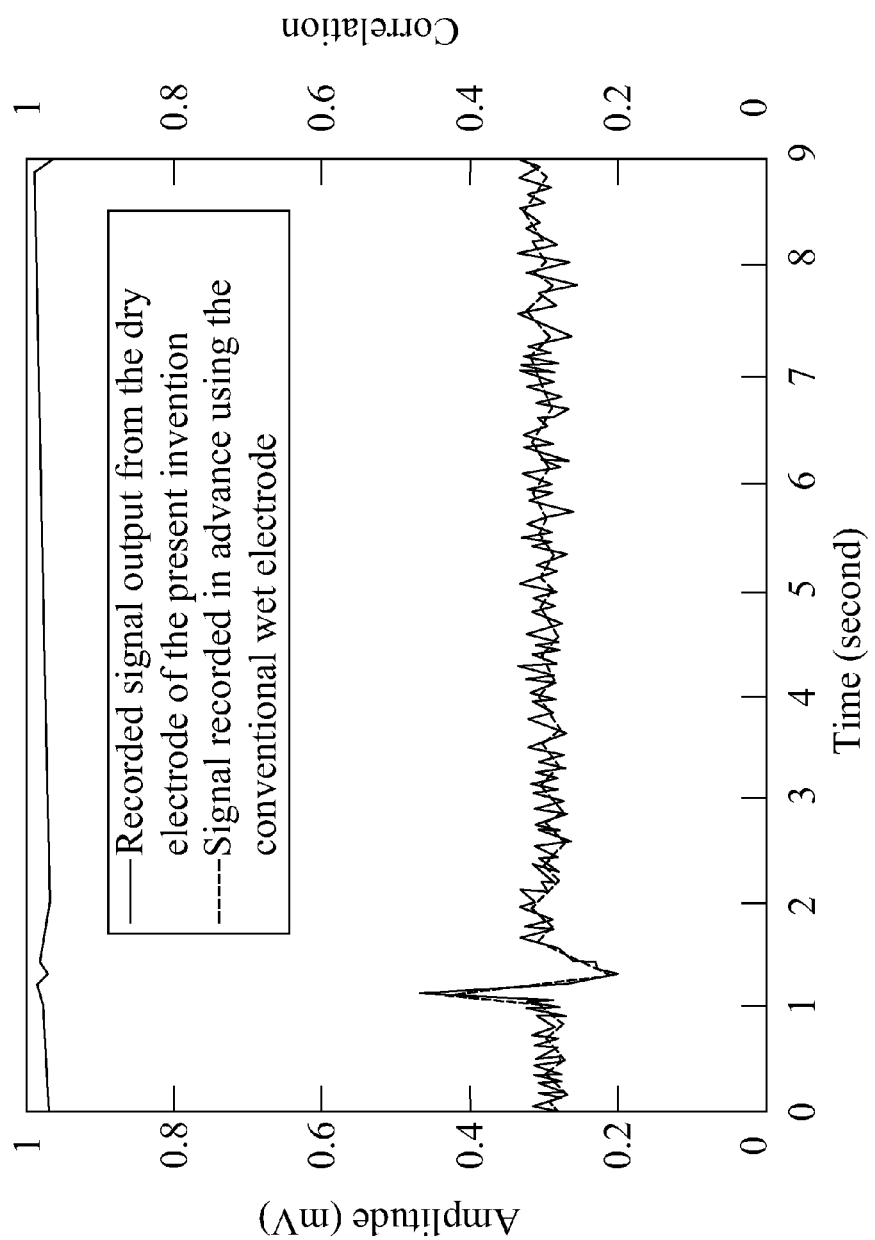
FIG. 3 shows a waveform obtained in a signal quality test conducted on the dry electrode of the present invention.

The purpose of the signal quality check is to understand whether there is any distortion in the data measured by the dry electrode of the present invention when the same is used in detecting brain wave signal. First, use the standard wet electrodes for an electroencephalograph (EEG) to record brain wave data in advance and store the same in a computer. Then, transmit the recorded brain wave data to a programmable function generator to generate a simulated EEG signal via a voltage divider. The simulated EEG signal is then transmitted to the dry electrode of the present invention and amplified by a brain wave signal amplifier. The amplified EEG signal is recorded and then compared with the brain wave data. FIG. 3 shows the comparison result. As shown, a correlation between the brain wave data as measured with the standard wet electrodes for EEG and the counterparts as recorded with the dry electrodes of the present invention is as high as 99.86%. Thus, the above signal quality check proves that the biomedical signal measured with the dry electrode of the present invention does not have any distortion.

(B) Impedance Measurement

To measure a skin-electrode impedance of the dry electrode of the present invention, the two types of electrodes, namely, the dry electrode of the present invention and the conventional wet electrode, are placed on a patient's forehead and on the patient's back of head with the two types of electrodes spaced from one another by 4 cm. Before placing the electrodes on the areas to be measured, the skin at the areas is first cleaned with cotton swabs soaked with 2-propanol. Wait until the 2-propanol on the skin is completely volatized, and then place the electrodes on the patient's forehead and back of head. Then, apply electric current to the two electrodes for measuring the impedance thereof. Further, in measuring the skin-electrode impedance of the wet electrode, a conductive gel is applied on the patient's skin before the conventional wet electrode is placed thereon; and, both the skin-electrode impedances before and after the stratum corneum is removed from the skin of the measured area will be measured. On the other hand, in measuring the skin-electrode impedance of the dry electrode of the present invention, the impedance is measured without removing the stratum corneum from the skin of the measured area and without applying any conducting gel on the skin of the measured area.

Figure 4:
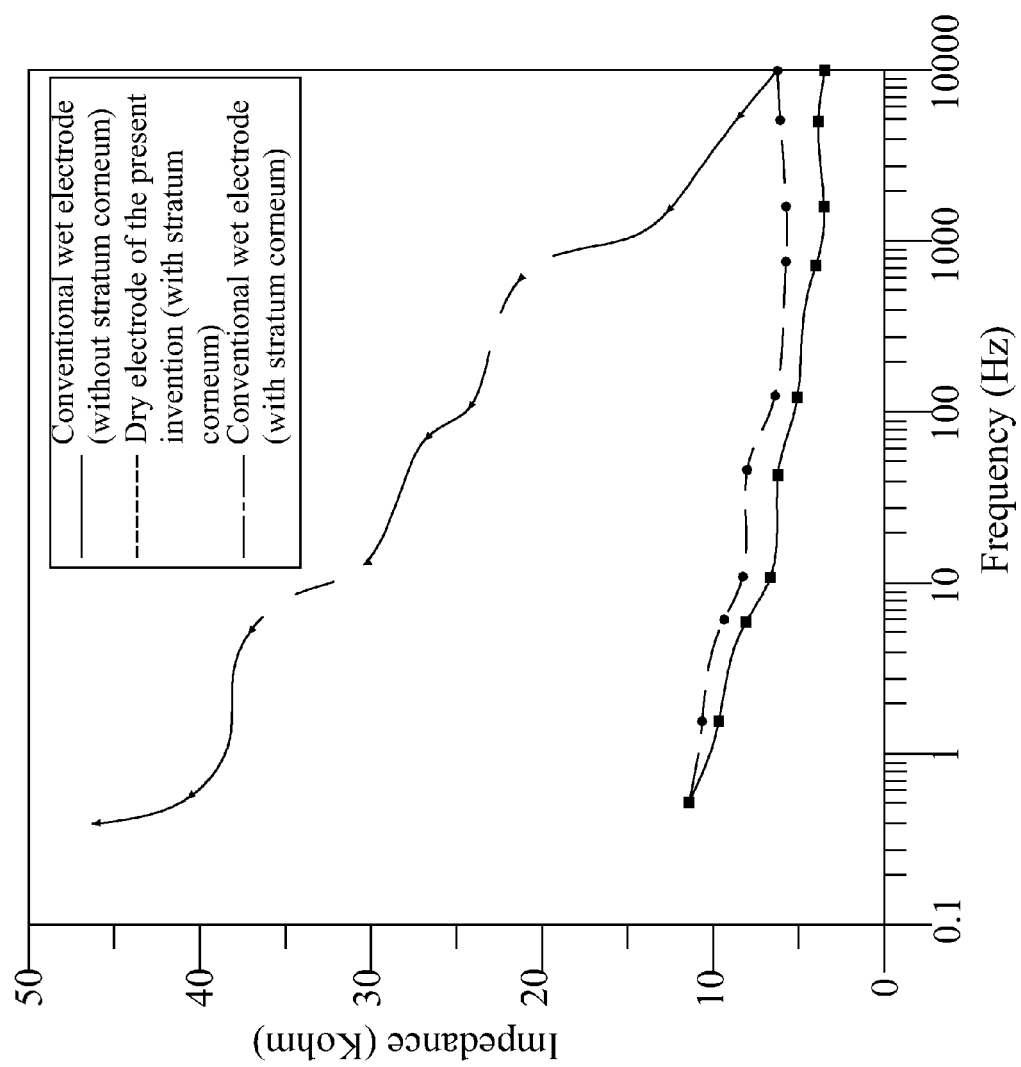
FIG. 4 is a diagram showing impedances of the dry electrode of the present invention and the conventional wet electrode when they are placed on a patient's forehead.

Please refer to FIG. 4 that shows the skin-electrode impedances of the dry electrode of the present invention and the conventional wet electrode when they are placed on the patient's forehead. As shown, the impedance between the stratum-corneum-existing and conductive-gel-free forehead skin and the dry electrode of the present invention is approximate to the impedance between the stratum-corneum-removed and conductive-gel-applied forehead skin and the conventional wet electrode. Therefore, it is proven the dry electrode of the present invention is more convenient for use because it is not necessary to apply the conductive gel and remove the stratum corneum before the dry electrode is placed on the skin. In addition, in the case the conventional wet electrode is placed on a skin area with stratum corneum; the measured impedance thereof is apparently unstable. Therefore, the dry electrode of the present invention has conduction performance superior to that of the conventional wet electrode.

Figure 5:
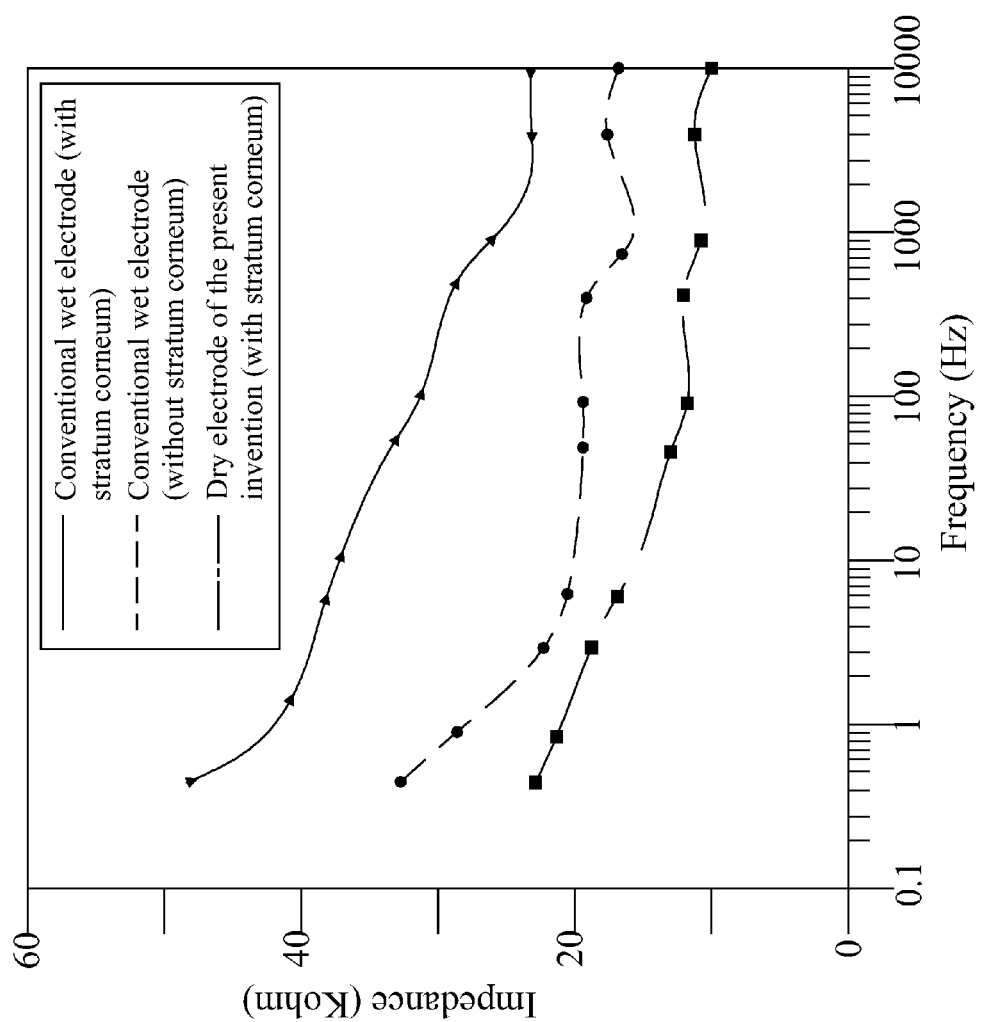
FIG. 5 is a diagram showing impedances of the dry electrode of the present invention and the conventional wet electrode when they are placed on a patient's back of head.

Please refer to FIG. 5 that shows the skin-electrode impedances of the dry electrode of the present invention and the conventional wet electrode when they are placed on the patient's back of head. As shown, the impedance between the dry electrode and the back of head is similar to that between the dry electrode and the forehead skin while the latter is lower than the former. Apparently, the dry electrode of the present invention is relatively soft and is soft enough to fitly attach to the skin of the patient's back of head. The conductive fabric used in the dry electrode of the present invention is also highly electrically stable. Compared to the conventional wet electrode, the dry electrode of the present invention can be used to accurately measure biomedical signal without the need of removing the stratum corneum from the skin and applying the conductive gel on the skin.

Figure 6:
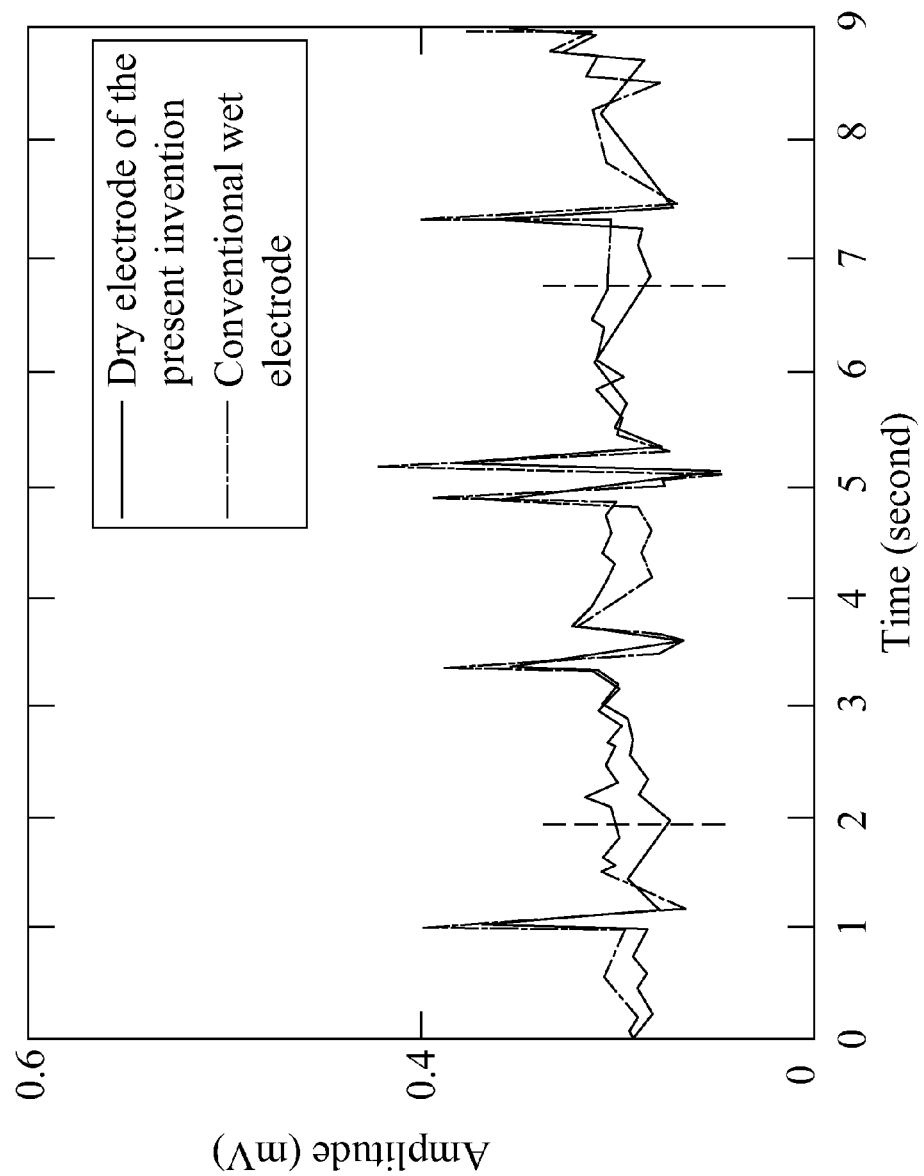
FIG. 6 shows waveforms of biomedical signals separately measured via the dry electrode of the present invention and the conventional wet electrode when they are placed on a patient's forehead.
Figure 7:
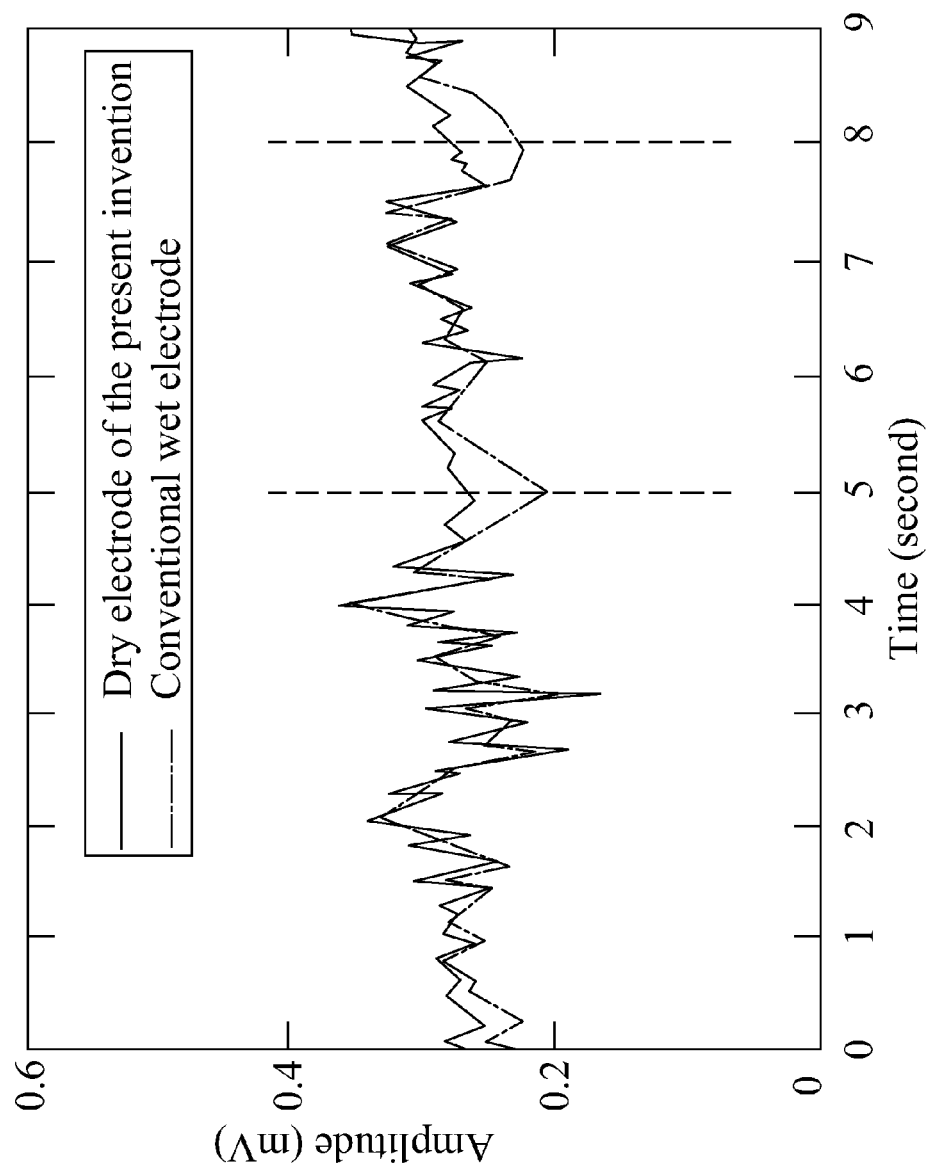
FIG. 7 shows waveforms of biomedical signals separately measured via the dry electrode of the present invention and the conventional wet electrode when they are placed on a patient's back of head.

(C) Motion Artifact Test In this test, the influence of the two different types of electrodes on the biomedical signal measured in movement will be checked. In the first 15 minutes of the test, the biomedical signal measured with the conventional wet electrode is stable. However, after 17 minutes, when the conductive gel gradually becomes dried with time, more motion artifacts (not shown) appear in the signal measured with the conventional wet electrode compared to the signal measured with the dry electrode of the present invention Please refer to FIGS. 6 and 7 that show biomedical signals measured with the dry electrode of the present invention and the conventional wet electrode by placing the two electrodes on the patient's forehead and back of head, respectively. As can be seen from both figures, the number of motion artifacts in the biomedical signals measured with the dry electrode of the present invention is obviously smaller than that in the biomedical signals measured with the conventional wet electrode. Particularly, the signals measured at the patient's forehead with the conventional wet electrode at 2 seconds and 6.5 second as marked by phantom lines shown in FIG. 6 and the signals measured at the patient's back of head with the conventional wet electrode at 5 seconds and 8 seconds as marked by phantom lines shown in FIG. 7 are unstable. On the other hand, the biomedical signals measured on the patient's skin at forehead and back of head using the dry electrode of the present invention are relatively consistent with each other. This proves that the dry electrode of the present invention can be more fitly attached to the patient's skin compared to the conventional wet electrode, and the biomedical signal measured with the dry electrode of the present invention is more stable than that measured with the conventional wet electrode.

Figure 8:
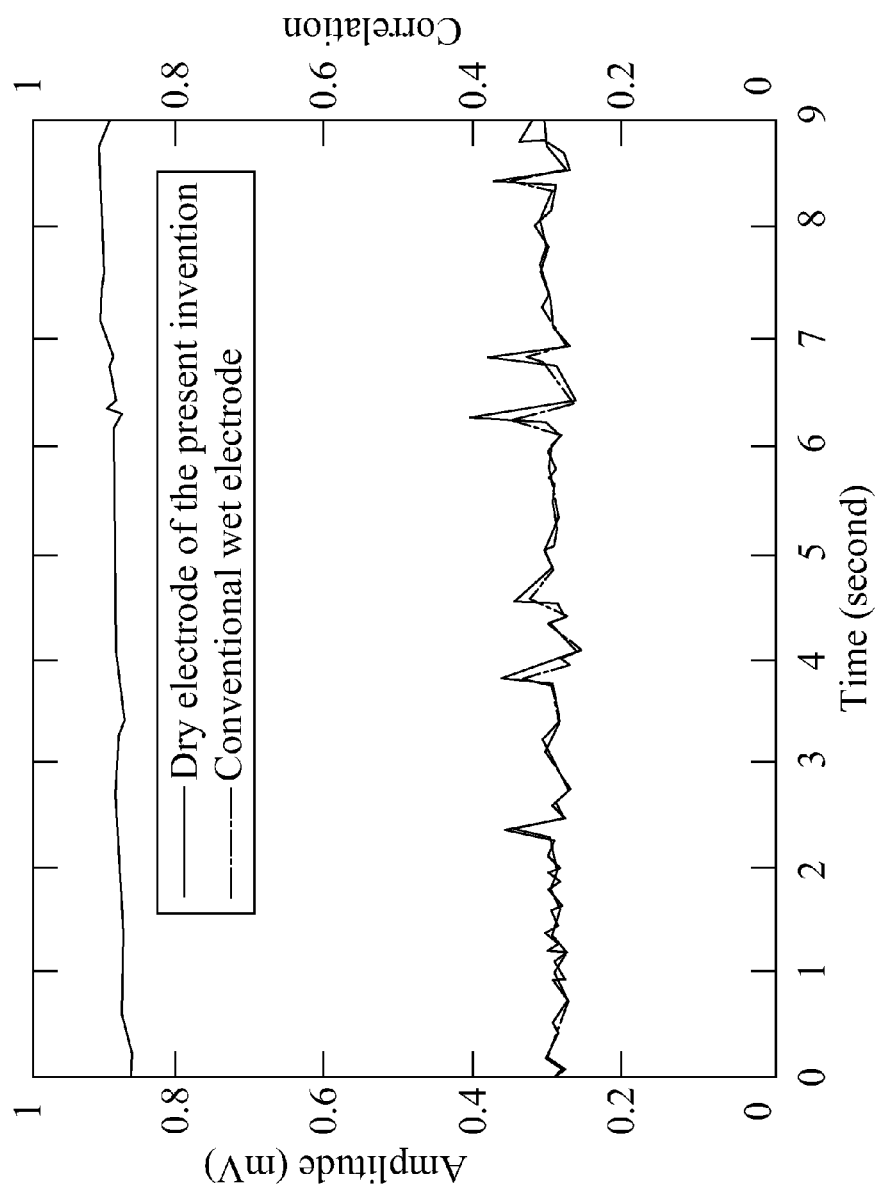
FIG. 8 compares the waveforms of the biomedical signals separately measured via the dry electrode of the present invention and the conventional wet electrode when they are placed on a patient's forehead.

(D) Comparison of Signals Measured with the Dry Electrode of the Present Invention and the Conventional Wet Electrode Signals separately measured at the patient's forehead, lateral side of head with hair, and eye (for measuring eye movement signal) using the dry electrode of the present invention and the conventional wet electrode are compared. The comparison results at three different areas are respectively shown in FIGS. 8 to 10. As shown in FIG. 8, there is not significant difference between the signals measured at the patient's forehead using the dry electrode of the present invention and the conventional wet electrode. The signals measured at the patient's forehead consist of many eye movement signals, and each peak in the waveforms indicates one blink signal. A correlation coefficient between the two signals separately measured with the dry and the wet electrode as calculated using MATLAB is 0.9632.

Figure 9:
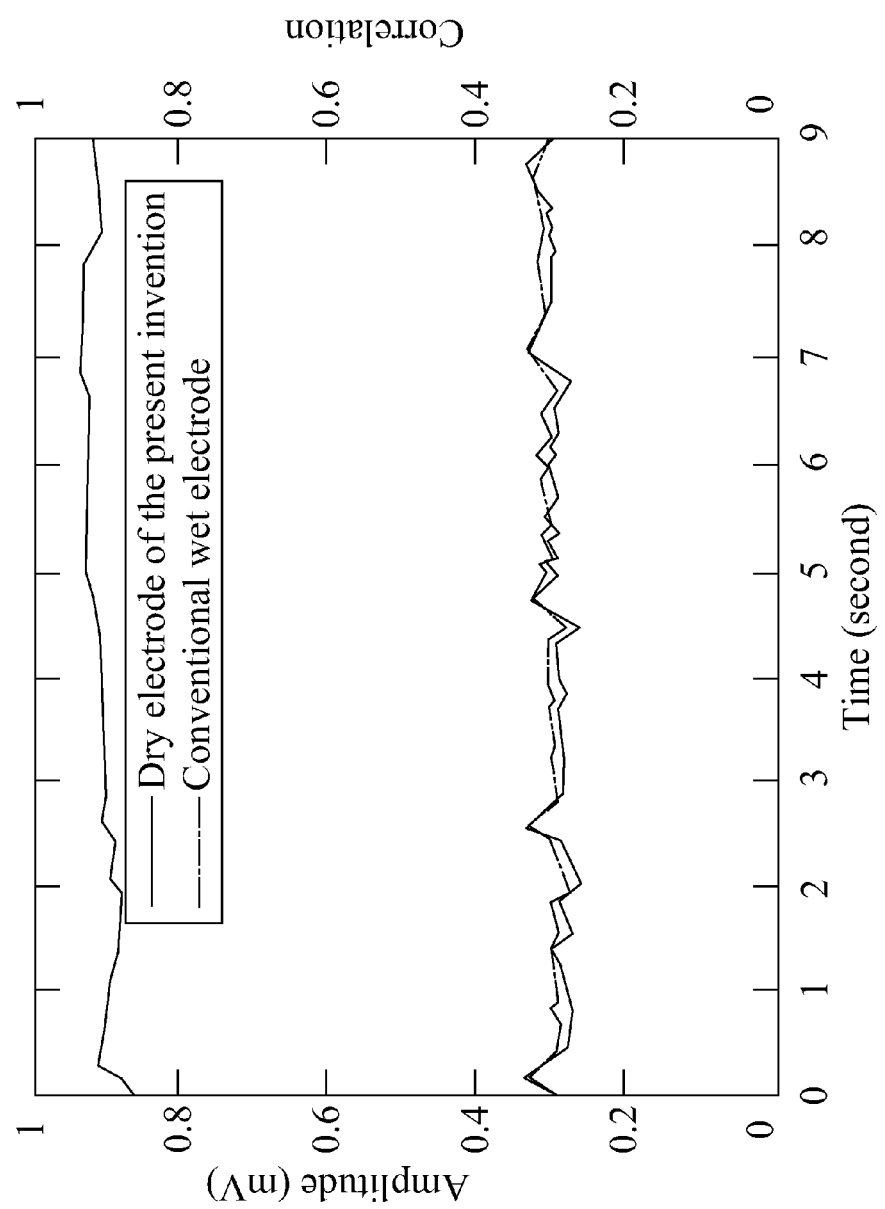
FIG. 9 compares the waveforms of the biomedical signals separately measured via the dry electrode of the present invention and the conventional wet electrode when they are placed on a patient's back of head.
Figure 10:
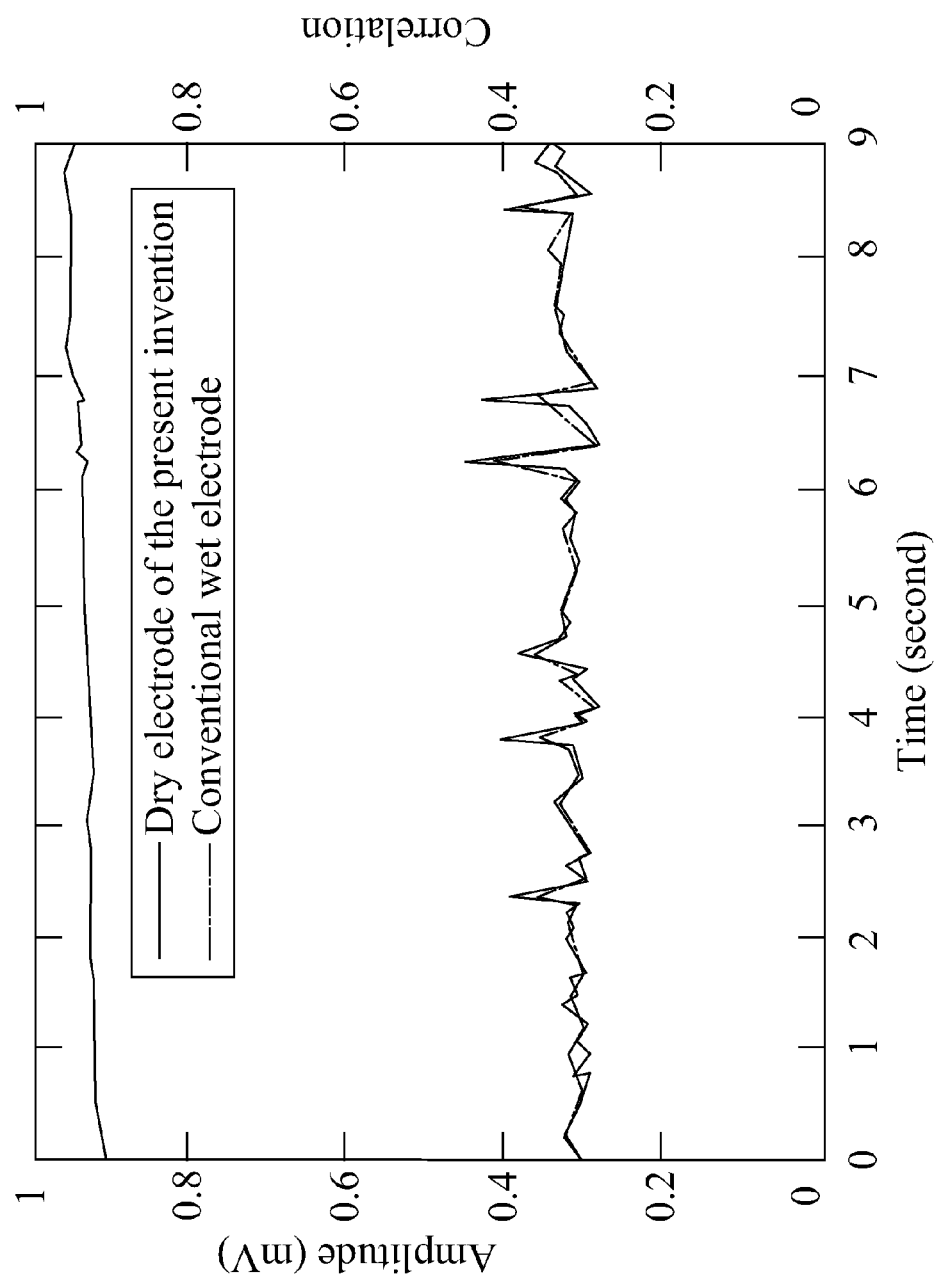
FIG. 10 compares the waveforms of the biomedical signals separately measured via the dry electrode of the present invention and the conventional wet electrode when they are placed on a patient's eye.

FIG. 9 compares the signals measured at the patient's lateral side of head with hair using the dry electrode of the present invention and the conventional wet electrode. As can be seen in FIG. 9, the measured signals do not show any significantly increased noise even if the measuring is affected by the hair, and the signals measured at this area is less influenced by the blink movement. Further, the signal measured with the dry electrode of the present invention is generally similar to that measured with the conventional wet electrode. A correlation coefficient between the two signals separately measured with the dry and the wet electrode as calculated using MATLAB is 0.9218. And, a correlation coefficient between the eye movement signals separately measured with the dry and the wet electrode as calculated using MATLAB is 0.9728. From the above experimental results, it is proven the signals measured with the dry electrode of the present invention is the same as those measured with the conventional wet electrode, and the dry electrode of the present invention is more convenient for use compared to the conventional wet electrode.

The dry electrode of the present invention can be used to measure not only brain wave signal and eye movement signal, but also other biomedical signals, such as muscle electric signal and heart electric signal. Moreover, the dry electrode of the present invention has very good pliability and can be very fitly attached to the patient's body area for measuring the biomedical signal. Even if the patient being measured is in movement, the use of the dry electrode of the present invention can still provide signal with good measurement characteristics. Further, since the use of the dry electrode of the present invention does not require the application of a conductive gel on the patient's skin, it would not cause discomforts, such as allergy and swelling, to the patient. The dry electrode of the present invention can be directly used at the patient's area having densely distributed hair to measure biomedical signal without the need of invading into the patient's skin or shaving the hair off the skin, and the measured biomedical signal would not attenuate with time. Therefore, compared to the conventional wet electrode, the dry electrode of the present invention is indeed more convenient for measuring different biomedical signals at any time.

The present invention has been described with some preferred embodiments thereof and it is understood that many changes and modifications in the described embodiments can be carried out without departing from the scope and the spirit of the invention that is intended to be limited only by the appended claims.

What is claimed is:

1. A dry electrode for biomedical signal measuring sensor, comprising:
    a conductive sponge;
    a conductive fabric being covered over the whole conductive sponge; and
    a thin metal film being disposed on one face of the conductive fabric opposite to the conductive sponge.

2. The dry electrode as claimed in claim 1, wherein the conductive sponge is made of a urethane material.

3. The dry electrode as claimed in claim 1, wherein the conductive fabric is in the form of a honeycomb net.

4. The dry electrode as claimed in claim 1, wherein the conductive fabric is a fabric coated with a layer of metal.

5. The dry electrode as claimed in claim 4, wherein the fabric is a taffeta fabric.

6. The dry electrode as claimed in claim 4, wherein the metal is selected from the group consisting of platinum, nickel, copper, aluminum, iron and silver.

7. The dry electrode as claimed in claim 1, wherein the thin metal film is formed of gold.

8. The dry electrode as claimed in claim 1, further comprising an enclosure made of an electromagnetic-shielding material, and the enclosure being provided around the conductive fabric that is covered on the whole conductive sponge.

* * * * *